(12) United States Patent
Simpson et al.

(10) Patent No.: US 11,596,462 B2
(45) Date of Patent: *Mar. 7, 2023

(54) SURGICAL INSTRUMENT AND METHOD

(71) Applicant: WARSAW ORTHOPEDIC, INC., Warsaw, IN (US)

(72) Inventors: Joshua W. Simpson, Collierville, TN (US); Jason M. May, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 497 days.

This patent is subject to a terminal disclaimer.

(21) Appl. No.: 16/790,005

(22) Filed: Feb. 13, 2020

(65) Prior Publication Data
US 2020/0179025 A1 Jun. 11, 2020

Related U.S. Application Data

(63) Continuation of application No. 15/551,518, filed as application No. PCT/US2016/018903 on Feb. 22, (Continued)

(51) Int. Cl.
*A61B 17/88* (2006.01)
*A61B 17/70* (2006.01)
(Continued)

(52) U.S. Cl.
CPC ...... *A61B 17/8869* (2013.01); *A61B 17/7034* (2013.01); *A61B 17/7053* (2013.01);
(Continued)

(58) Field of Classification Search
CPC ............ A61B 17/8869; A61B 17/7053; A61B 17/7076
See application file for complete search history.

(56) References Cited

U.S. PATENT DOCUMENTS 5,449,361 A   9/1995   Preissman
6,689,140 B2  2/2004   Cohen
(Continued)

FOREIGN PATENT DOCUMENTS

EP   2777569 A1   9/2014

OTHER PUBLICATIONS

European Search Report and Written Opinion of the International Searching Authority, European Patent Office, PCT/US2016/018903, dated Oct. 18, 2018.
(Continued)

*Primary Examiner* — Ellen C Hammond
(74) *Attorney, Agent, or Firm* — Sorell, Lenna & Schmidt, LLP

(57) ABSTRACT

A surgical instrument comprises a first member including a lateral projection having a locking surface that defines an elongated cavity. The locking surface is engageable with a longitudinal member to fix the longitudinal member with the first member. A second member includes at least one mating element being engageable with a spinal construct. The first member is axially translatable relative to the second member in a first direction to tension the longitudinal member and in a second direction to release tension from the longitudinal member. Systems and methods are disclosed.

20 Claims, 10 Drawing Sheets

Related U.S. Application Data 2016, now Pat. No. 10,595,920, which is a continuation of application No. 14/631,492, filed on Feb. 25, 2015, now abandoned.

(51) Int. Cl.
*A61B 17/84* (2006.01)
*A61B 17/00* (2006.01)

(52) U.S. Cl.
CPC ........ *A61B 17/7076* (2013.01); *A61B 17/842* (2013.01); *A61B 2017/00004* (2013.01)

(56) References Cited

U.S. PATENT DOCUMENTS

| | | | |
|---|---|---|---|
| 8,162,946 B2* | 4/2012 | Baccelli | A61B 17/8869 606/86 A |
| 8,814,910 B2 | 8/2014 | Baccelli et al. | |
| 8,870,881 B2 | 10/2014 | Rezach et al. | |
| 2006/0089651 A1 | 4/2006 | Trudeau et al. | |
| 2013/0072983 A1 | 3/2013 | Lindquist et al. | |
| 2014/0277207 A1 | 9/2014 | Baccelli et al. | |

OTHER PUBLICATIONS

IP Australia Examination report No. 1 for standard patent application, Application No. 2016222998, dated Aug. 5, 2019.
China National Intellectual Property Administration, Notice on the First Office Action, 201680009576.1, dated Aug. 1, 2019 and translation thereof.
China National Intellectual Property Administration, OfficeAction—China—2017543926 and translation thereof.
Documents mailed from International Searching Authority, ISA/KR Jul. 25, 2016, International Application Division, Korean intellectual Properly Office, 189 Cheongsa-ro, Seo-gu, Daejeon, Republic of Korea; Form PCT/ISA/210 International Search Report ; ORM PCT/ISA/237 Written Opinion of the International Searching Authority (Korean Patent Office).

\* cited by examiner

SURGICAL INSTRUMENT AND METHOD

CROSS REFERENCE TO RELATED APPLICATIONS

This application is a continuation of U.S. patent application Ser. No. 15/551,518, filed on Aug. 16, 2017, which is hereby expressly incorporated herein by reference, in its entirety.

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods, bone screws and sub-laminar wire, for stabilization of a treated section of a spine. This disclosure describes an improvement over these prior art technologies.

SUMMARY

In one embodiment, a surgical instrument comprises a first member including a lateral projection having a locking surface that defines an elongated cavity. The locking surface is engageable with a longitudinal member to fix the longitudinal member with the first member. A second member includes at least one mating element being engageable with a spinal construct. The first member is axially translatable relative to the second member in a first direction to tension the longitudinal member and in a second direction to release tension from the longitudinal member. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
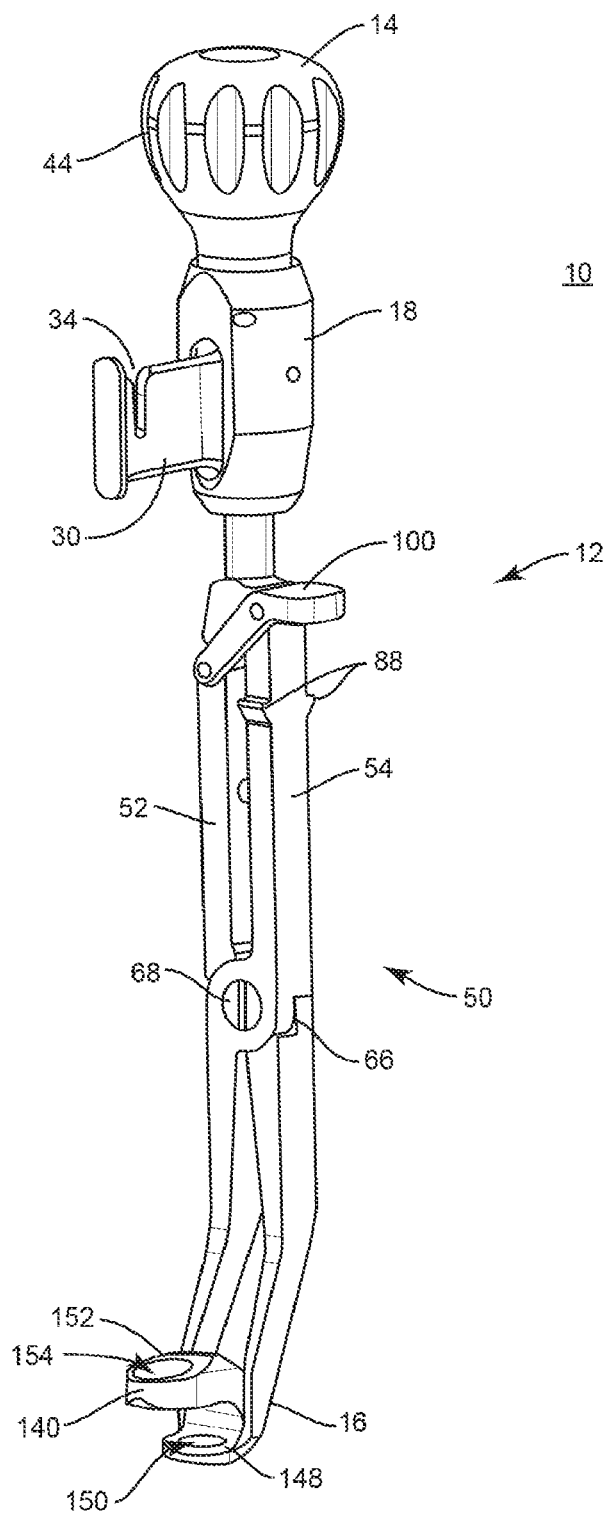
FIG. 1 is a perspective view of one embodiment of components of a surgical system in accordance with the principles of the present disclosure.

The exemplary embodiments of a surgical system and related methods of use are discussed in terms of medical devices for the treatment of musculoskeletal disorders and more particularly, in terms of a surgical system and method for correction of a spine disorder. In some embodiments, the surgical system may be employed in applications for correction of deformities, such as scoliosis and kyphosis.

In some embodiments, the surgical system includes a surgical instrument configured to apply a tension to a sublaminar tether. In some embodiments, the surgical system includes a tensioner configured to apply a tension to a tether and/or a spinal construct. In some embodiments, the tensioner is configured for attachment with a spinal construct, such as, for example, a connector. In some embodiments, the tensioner is configured for attachment with the connector via mating surfaces. In some embodiments, the mating surfaces include one or more slots. In one embodiment, the tensioner includes a mating element for engagement with slots disposed with the connector. In some embodiments, the tensioner comprises an implant holder.

In some embodiments, the surgical system includes a tether configured for engagement with the connector. In some embodiments, the tether is passed through the connector and engaged with a protrusion of a tensioning carriage disposed with the tensioner. In one embodiment, the tether is wrapped around the protrusion on the tensioning carriage. In some embodiments, an end of the tether is disposed with a slot in an end of the protrusion to prevent the tether from unwrapping. In some embodiments, a tension of the tether fixes the tether with the protrusion.

In some embodiments, the surgical instrument includes a threaded shaft to facilitate translation of a carriage in a direction away from the connector by rotation along a threaded shaft. In some embodiments, the surgical instrument includes a knob to actuate translation and apply a tension to the tether.

In some embodiments, the surgical system is used with surgical navigation, such as, for example, fluoroscope or image guidance. In one embodiment, one or all of the components of the surgical system are disposable, peel-pack, pre-packed sterile devices. One or all of the components of the surgical system may be reusable. The surgical system may be configured as a kit with multiple sized and configured components.

In one embodiment, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In one embodiment, the present disclosure may be employed with other osteal and bone related applications, including those associated with diagnostics and therapeutics. In some embodiments, the disclosed surgical system and methods may be alternatively employed in a surgical treatment with a patient in a prone, supine position, lateral and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to exemplary embodiments of the present disclosure, which are illustrated in the accompanying figures. Turning to FIGS. 1-12, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites. For example, the components of spinal correction system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 comprises a surgical instrument, such as, for example, a tensioner 12. Tensioner 12 extends between an end 14 and an end 16. Tensioner 12 defines a longitudinal axis X1. In some embodiments, tensioner 12 may comprise overall and/or cross-section configurations, such as, for example, cylindrical, round, oval, rectangular, polygonal, irregular, tapered, offset, staggered, uniform and non-uniform. In some embodiments, one or more of the surfaces of tensioner 12 may have alternate surface configurations, such as, for example, rough, threaded for connection with surgical instruments, arcuate, undulating, porous, semi-porous, dimpled, polished and/or textured.

Tensioner 12 includes a member, such as, for example, a carriage 18. Carriage 18 extends between an end 20 and an end 22. Carriage 18 has a circular cross-sectional configuration. In some embodiments, carriage 18 may have various configurations, for example, cylindrical, square, oval, rectangular, polygonal, irregular, tapered, offset, staggered and uniform. Carriage 18 includes an outer surface 24. Outer surface 24 has a smooth surface configuration. In some embodiments, outer surface 24 may have alternate surface configurations, such as, for example, rough, threaded for connection with surgical instruments, arcuate, undulating, porous, semi-porous, dimpled, polished and/or textured.

Figure 2:
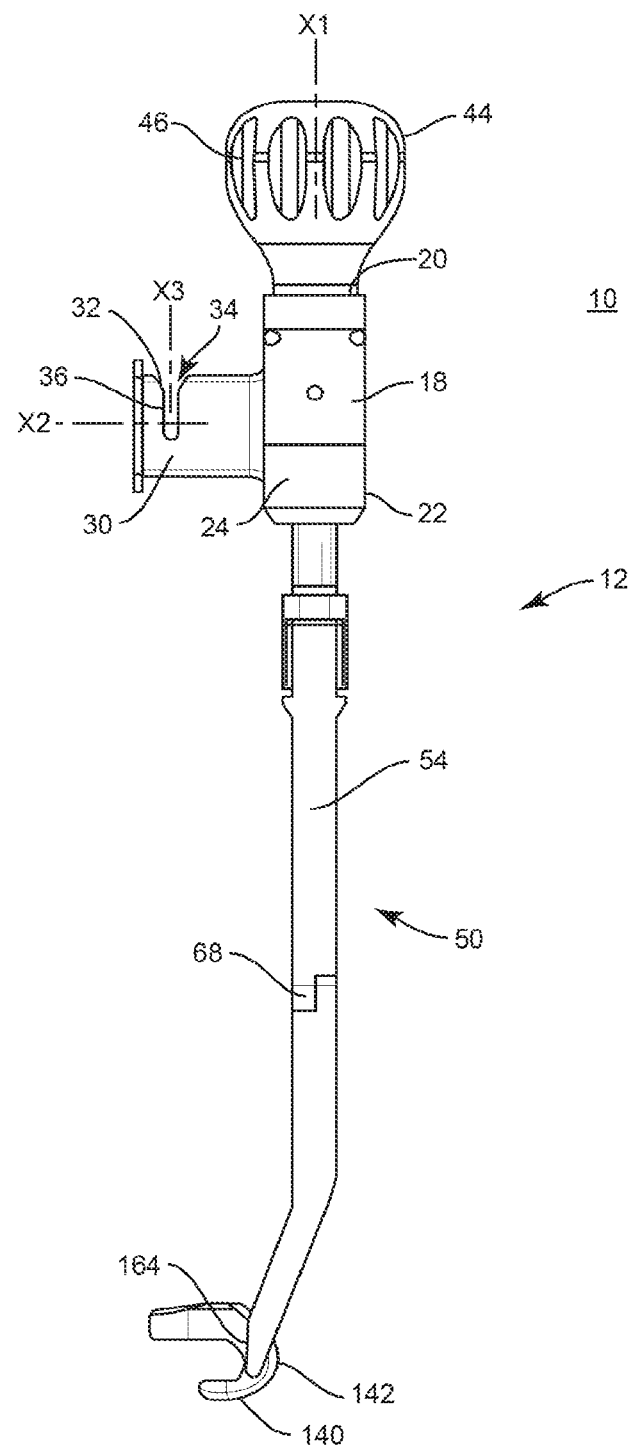
FIG. 2 is a side view of the components shown in FIG. 1.
Figure 3:
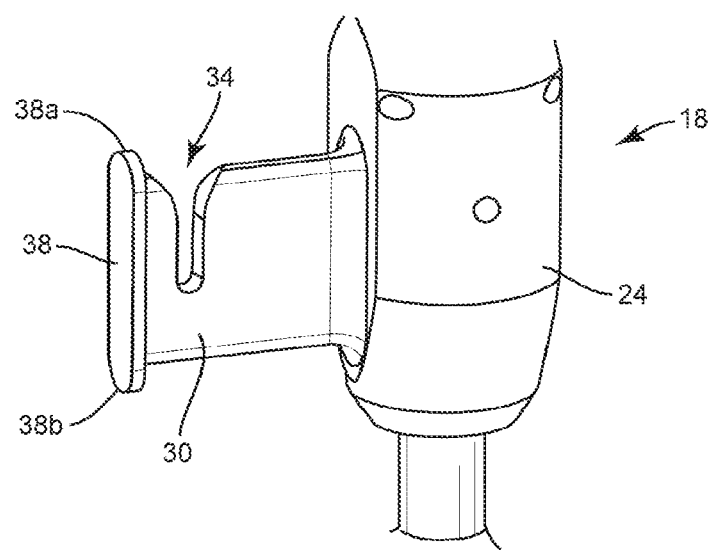
FIG. 3 is a break away view of the components shown in FIG. 1.
Figure 4:
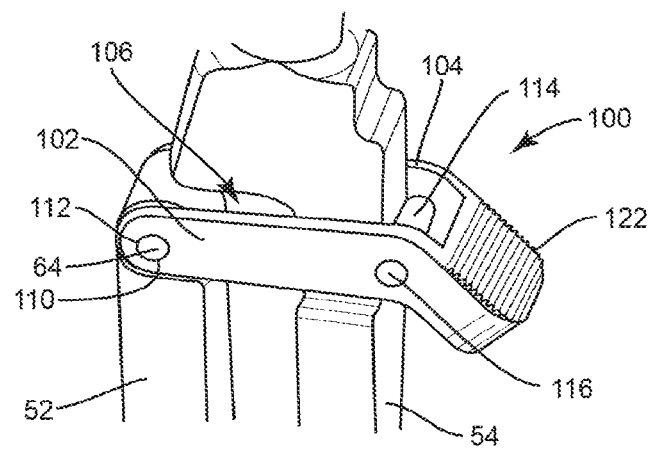
FIG. 4 is a break away view of the components shown in FIG. 1.
Figure 5:
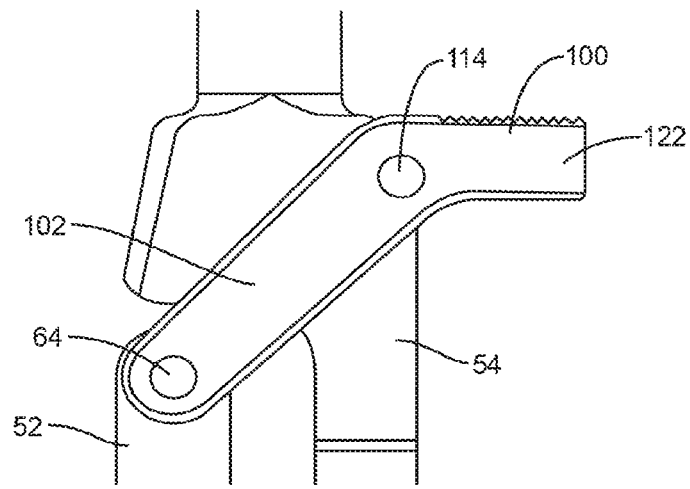
FIG. 5 is a break away view of the components shown in FIG. 1.
Figure 6:
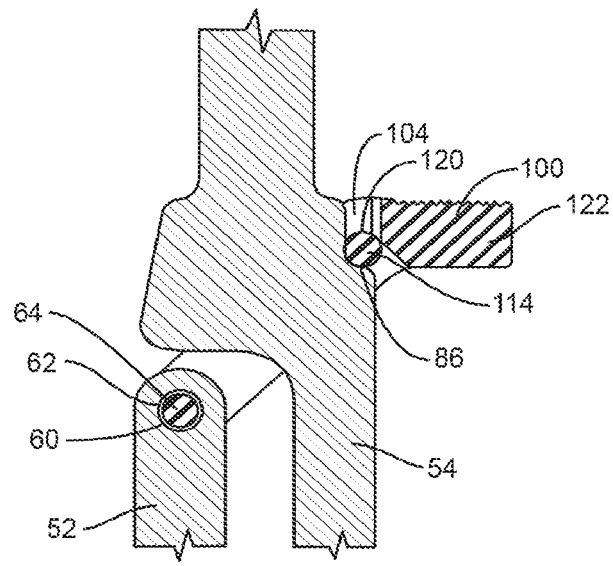
FIG. 6 is a cross section view of the components shown in FIG. 5.
Figure 7:
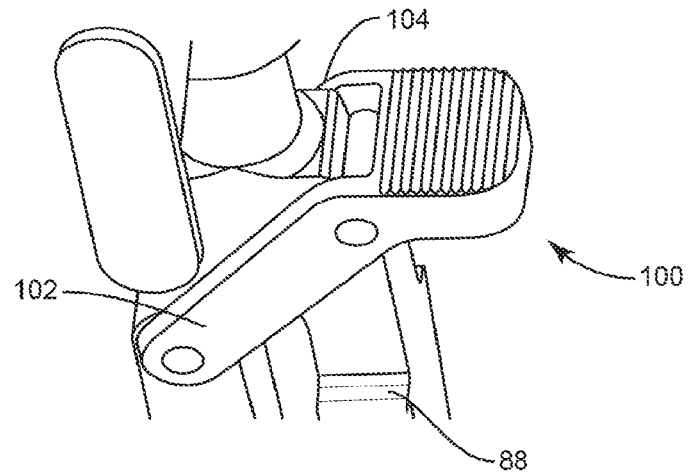
FIG. 7 is a break away view of the components shown in FIG. 1.

Carriage 18 includes a projection 30 extending laterally from surface 24. Projection 30 includes a flat and/or even surface profile and defines an axis X2 extending transverse to axis X1, as shown in FIG. 2. Projection 30 includes a locking surface 32 configured for engagement with a longitudinal member, such as, for example, a tether 130, as described herein. Locking surface 32 defines an elongated cavity, such as, for example, a slot 34. Slot 34 extends along an axis X3. In some embodiments, axis X3 is parallel to axis X1. In some embodiments, axis X3 extends transverse to axis X1. In one embodiment, as shown in FIG. 2, slot 34 includes a tapered portion 36 configured to receive tether 130 and provisionally fix tether 130 with projection 30. In some embodiments, slot 34 may have various configurations, for example, square, oval, rectangular, polygonal, irregular, offset, staggered, uniform and non-uniform.

Projection 30 includes a flange 38 that extends along a width of projection 30. Flange 38 is configured to form extensions 38a, 38b configured to prevent and/or limit lateral movement of tether 130 along projection 30 to resist and/or prevent disengagement and/or release of tether 130 from projection 30.

Figure 12:
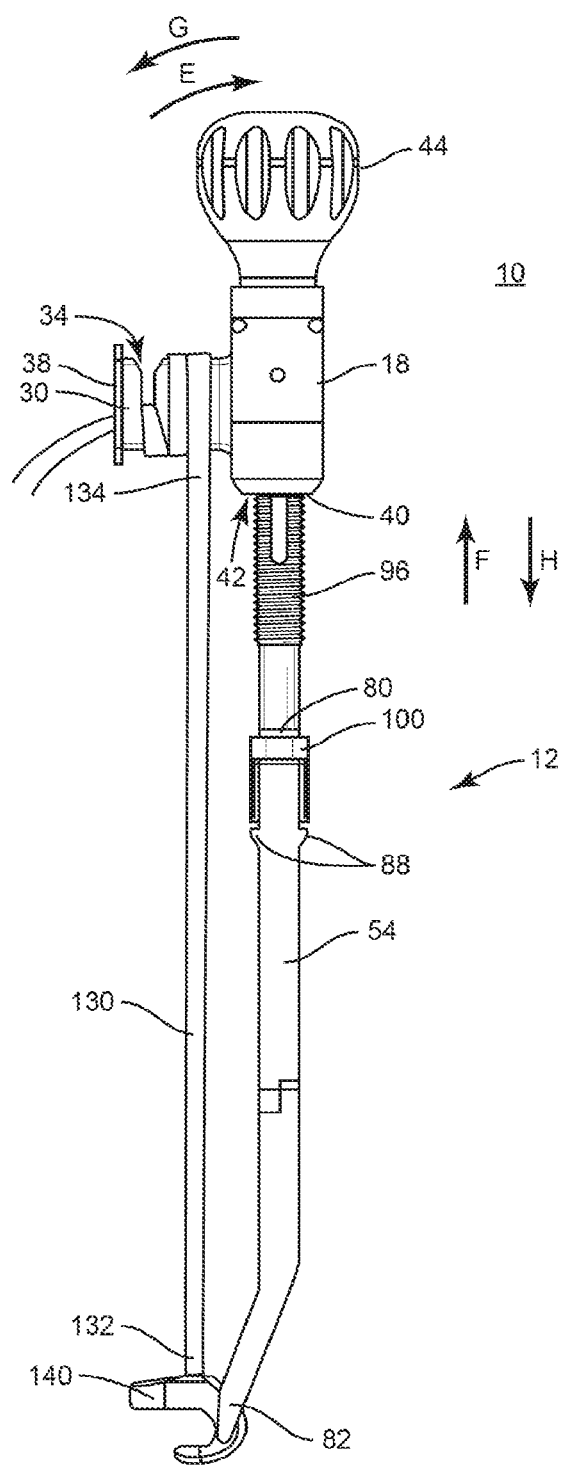
FIG. 12 is a side view of the components shown in FIG. 11.

Carriage 18 includes an inner threaded surface 40, as shown in FIG. 12. Surface 40 defines a translation cavity 42 that extends through at least a portion of carriage 18. Cavity 42 extends along longitudinal axis X1. Cavity 42 is configured for engagement and axial translation along a threaded shaft 96 of an arm 54, as described herein.

Carriage 18 is connected with an actuator, such as, for example, a knob 44. In one embodiment, knob 44 is rotatable to facilitate axial translation of carriage 18 relative to an engagement member 50, as described herein. Knob 44 includes a surface 46 configured to facilitate gripping and rotation. In some embodiments, surface 46 may have alternate surface configurations, such as, for example, grooved, rough, threaded for connection with surgical instruments, arcuate, undulating, porous, semi-porous, dimpled, polished and/or textured.

Tensioner 12 includes engagement member 50 connected with carriage 18. Member 50 includes an arm 52 and an arm 54. Arm 52 extends between a proximal end 56 and a distal end 58. In some embodiments, the cross-section of arm 52 may have various configurations, such as, for example, round, oval, rectangular, polygonal, irregular, tapered, offset, staggered, uniform and non-uniform.

Arm 52 includes a surface 60 that defines a cavity 62 configured for disposal of a pin 64 of a lock 100, as described herein. In one embodiment, cavity 62 is disposed at proximal end 56. Arms 52, 54 define an opening, such as, for example, a channel 66 configured for disposal of a hinge 68. Arm 52 is rotatable about hinge 68 causing arm 52 to pivot relative to arm 54 to facilitate release, capture and/or locking of a spinal construct, such as, for example, a connector 140, as described herein, with engagement member 50. Hinge 68 is centrally disposed on arms 52, 54 and configured to facilitate rotation of arm 52 relative to arm 54. In some embodiments, hinge 68 may be variously configured, such as, for example, a pin, post, screw, living hinge, ratchet and/or concentric parts.

Arm 52 includes a surface 70 that defines a capture element, such as, for example, an elongated tab 72. Tab 72 is configured to engage connector 140. Surface 70 defines a portion of an engagement cavity 74 of tensioner 12. In some embodiments, surface 70 may have alternate surface configurations, such as, for example, rough, threaded for connection with surgical instruments, arcuate, undulating, porous, semi-porous, dimpled, polished and/or textured.

Arm 54 extends between a proximal end 80 and a distal end 82. In some embodiments, the cross-section of arm 54 may have various configurations, such as, for example, round, oval, rectangular, polygonal, irregular, tapered, offset, staggered, uniform and non-uniform.

Figure 8:
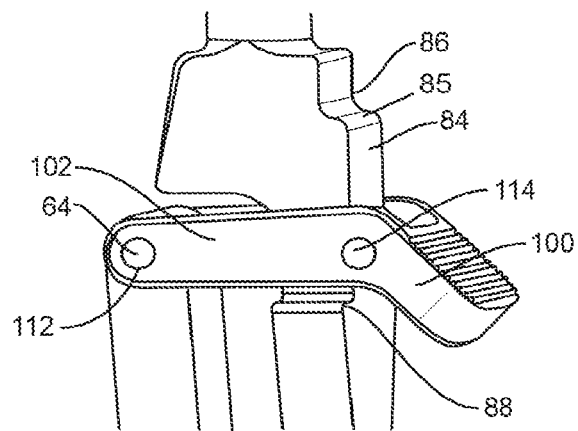
FIG. 8 is a break away view of the components shown in FIG. 1.

Arm 54 includes a surface 84. Surface 84 defines an engagement portion that includes a notch 86 and barbs 88. Notch 86 is configured for engagement with a pin 114 of lock 100 to fix arm 52 relative to arm 54, as described herein. Barbs 88 are disposed distally from notch 86 and are configured to limit movement of lock 100 to prevent arms 52, 54 from pivoting beyond a selected distance causing disengagement from connector 140. Pin 114 translates from engagement with notch 86 along surface 84 to engage barbs 88 to facilitate pivoting of arm 52 relative to arm 54. In some embodiments, pin 114 translates from engagement with notch 86 along surface 84 such that arm 52 and/or arm 54 bend and/or flex as pin 114 translates over rounded surface 85, as shown in FIG. 8. This configuration provides a snap and/or over-center mechanism of lock 100.

Arm 54 includes a surface 92 that defines a capture element, such as, for example, an elongated tab 94. Tab 94 is configured to engage connector 140. Surface 92 defines a portion of engagement cavity 74 of tensioner 12. In some embodiments, surface 92 may have alternate surface configurations, such as, for example, rough, threaded for connection with surgical instruments, arcuate, undulating, porous, semi-porous, dimpled, polished and/or textured.

Arm 54 includes a threaded shaft 96 extending from end 80 configured for engagement with carriage 18 to facilitate translation of carriage 18 relative to engagement member 50. Translation of carriage 18 relative to engagement member 50 in a direction opposite to connector 140 causes an increase in tension and/or tensile force in tether 130, as described herein. Translation of carriage 18 relative to engagement member 50 in a direction towards connector 140 causes a release of and/or decrease in tension and/or tensile force in tether 130.

Tensioner 12 includes lock 100. Lock 100 includes extensions 102, 104. Extensions 102, 104 form a cavity 106 for moveable disposal of arms 52, 54. Extension 102 includes a surface 110 that defines a cavity 112 configured for disposal of pin 64. Extension 104 defines a cavity (not shown), similar to cavity 112, configured for disposal of pin 64. Pin 64 extends between extensions 102, 104 through cavity 62 of arm 52. Rotation of pin 64 facilitates pivoting of arm 52 relative to arm 54.

Figure 9:
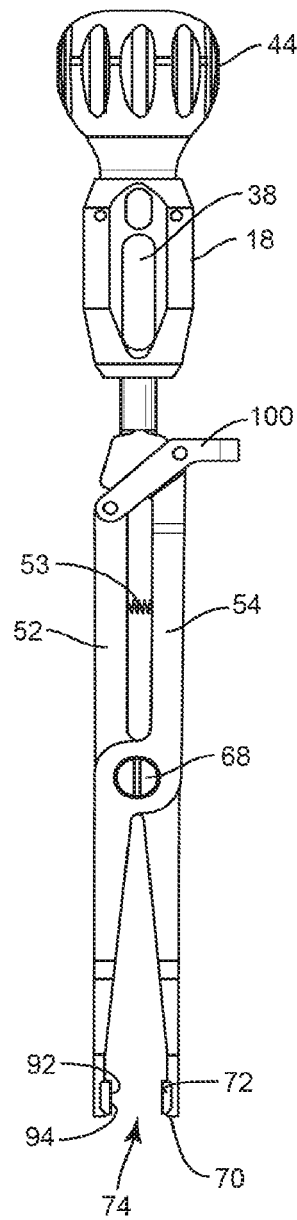
FIG. 9 is a side view of the components shown in FIG. 1.
Figure 10:
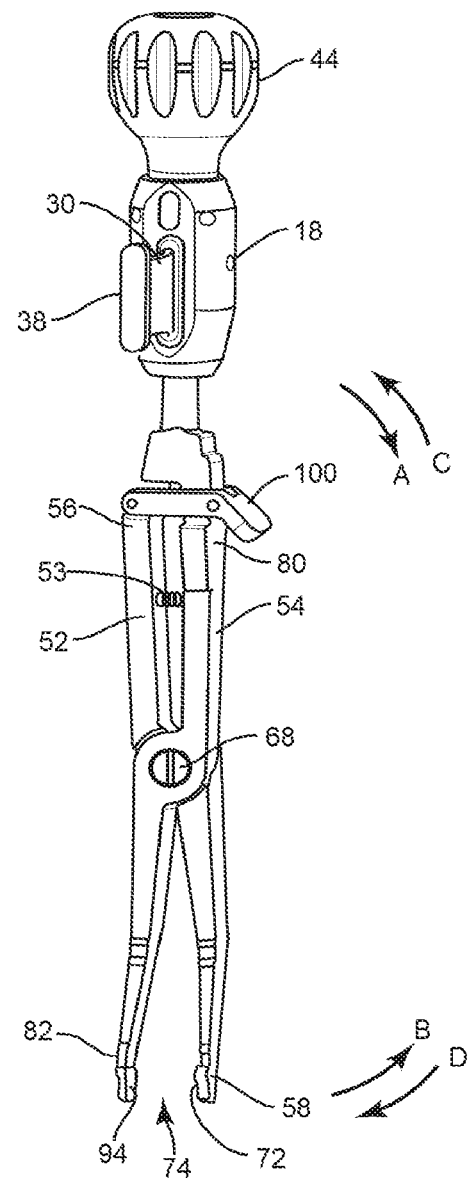
FIG. 10 is a perspective view of the components shown in FIG. 1.
Figure 11:
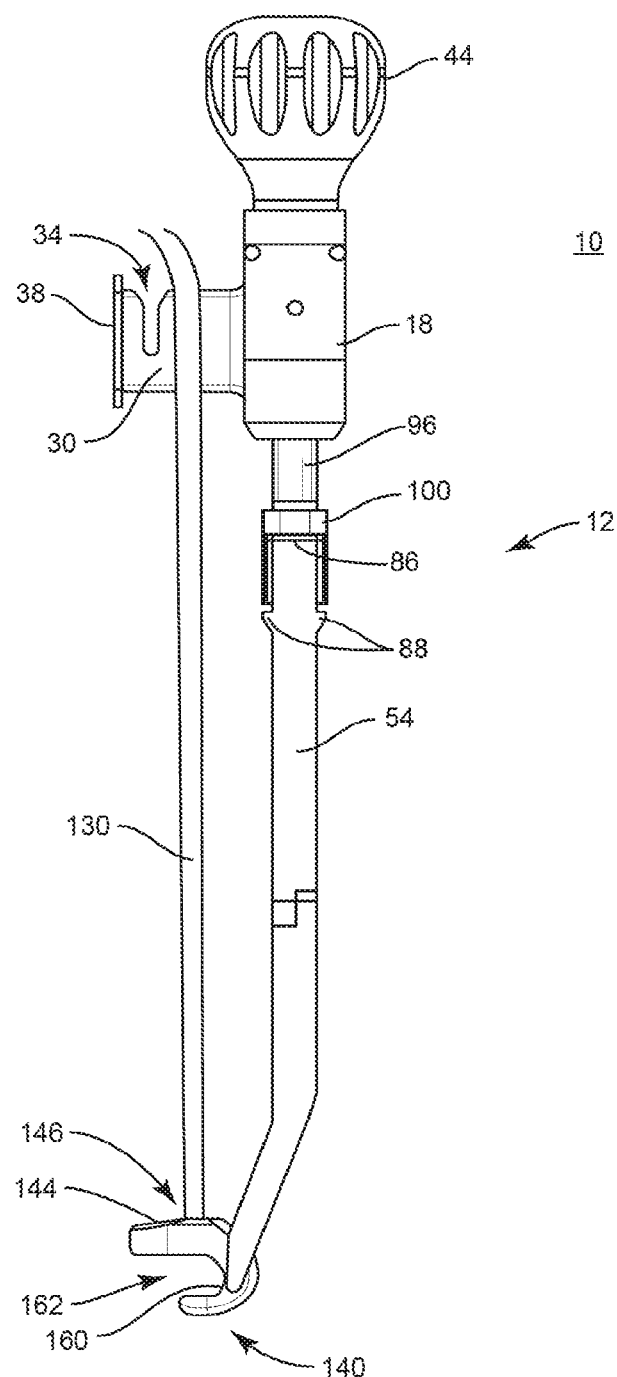
FIG. 11 is a side view of one embodiment of components of a surgical system in accordance with the principles of the present disclosure.

Surface 110 defines a cavity 116 configured for disposal of a pin 114. Extension 104 defines a cavity 120 configured for disposal of pin 114. Pin 114 extends between extensions 102, 104 and is disposed within cavity 106. Translation of pin 114 along the engagement portion of arm 54 causes lock 100 to move from notch 86 to barbs 88. This configuration facilitates movement of arms 52, 54 between an open orientation of tensioner 12, as shown in FIG. 10, such that arms 52, 54 are configured to receive and/or release a spinal construct, such as, for example, connector 140, and a closed orientation of tensioner 12, as shown in FIG. 9, such that arms 52, 54 capture connector 140. In the closed orientation, arms 52, 54 are releasably and/or provisionally fixed with connector 140, as shown in FIG. 1. In some embodiments, arms 52, 54 are resiliently biased to the open orientation via a biasing member, such as, for example, a spring 53. In some embodiments, the biasing member can include an elastic band, spring clip, telescoping shafts, resilient hinge or living hinge. In some embodiments, arms 52, 54 are not biased and manually manipulable to the orientations, as described herein.

Lock 100 includes an actuator, such as, for example, a tab 122 configured to facilitate translation of lock 100 along the engagement portion of arm 54 to dispose tensioner 12 between an open orientation and a closed orientation, as described herein. In some embodiments, the lock comprises a latch, and/or the arms include mating elements for engagement and capture of an implant. See also, the examples and disclosure of systems, surgical instruments, latches, arms, mating elements and methods shown and described in U.S. Provisional Patent Application No. Ser. No. 61/951,416 filed Mar. 11, 2014, the contents of which being hereby incorporated in its entirety by reference.

Spinal correction system 10 includes a longitudinal member, such as, for example, a tether 130. Tether 130 is a flexible longitudinal element that extends between an end 132 and an end 134. Tether 130 is configured for engagement with connector 140, as described herein. In some embodiments, end 132 and end 134 form a loop configured to surround all or a portion of tissue, such as, for example, laminae and/or a spinal implant, such as, for example, a spinal rod 170, as described herein. Tether 130 is configured for tensioning about a targeted portion of an anatomy of a body for attachment of tether 130 with the targeted portion of the anatomy, as described herein. In some embodiments, the targeted portion of the anatomy may include laminae, transverse process and/or pedicle regions of a vertebral level. In some embodiments, spinal correction system 10 may include one or a plurality of tethers 130, each tether being configured for disposal about a single and separate vertebral level. In some embodiments, a single vertebral level may include one or a plurality of tethers 130.

Tether 130 has a flexible configuration and may be fabricated from materials, such as, for example, fabric, silicone, polyurethane, silicone-polyurethane copolymers, polymeric rubbers, polyolefin rubbers, elastomers, rubbers, thermoplastic elastomers, thermoset elastomers and elastomeric composites. In one embodiment, the flexibility of tether 130 includes movement in a lateral or side to side direction and prevents expanding and/or extension in an axial direction upon tensioning and attachment with a targeted portion of the anatomy. In some embodiments, all or only a portion of tether 130 may have a semi-rigid, rigid or elastic configuration, and/or have elastic properties, similar to the material examples described above, such that tether 130 provides a selective amount of expansion and/or extension in an axial direction. In some embodiments, tether 130 may be compressible in an axial direction. Tether 130 can include a plurality of separately attachable or connectable portions or sections, such as bands or loops, or may be monolithically formed as a single continuous element.

Tether 130 can have a uniform thickness/diameter. In some embodiments, tether 130 may have various surface configurations, such as, for example, smooth and/or surface configurations to enhance fixation, such as, for example, rough, arcuate, undulating, porous, semi-porous, dimpled, polished and/or textured. In some embodiments, the thickness defined by tether 130 may be uniformly increasing or decreasing, or have alternate diameter dimensions along its length. In some embodiments, tether 130 may have various cross section configurations, such as, for example, oval, oblong, triangular, rectangular, square, polygonal, irregular, uniform, non-uniform, variable and/or tapered. In some embodiments, the surface of tether 130 may include engaging structures, such as, for example, barbs, raised elements and/or spikes to facilitate engagement with tissue of the targeted anatomy.

In some embodiments, tether 130 may have various lengths. In some embodiments, tether 130 may be braided, such as a rope, or include a plurality elongated elements to provide a predetermined force resistance. In some embodiments, tether 130 may be made from autograft and/or allograft, and be configured for resorbable or degradable applications. In one embodiment, tether 130 is a cadaver tendon. In one embodiment, tether 130 is a tendon that may be harvested, for example, from a patient or donor. In some embodiments, a tendon harvested from a patient may be affixed in remote locations with the patient's body.

Spinal correction system 10 includes connector 140. Connector 140 includes a body 142 having a surface 144 that defines a cavity, such as, for example, a passageway 146 configured for disposal of tether 130. In some embodiments, passageway 146 may have various cross section configurations, such as, for example, oval, oblong, triangular, rectangular, square, polygonal, irregular, uniform, non-uniform, variable and/or tapered. In some embodiments, surface 144 may include gripping elements or surfaces, such as, for example, rough, arcuate, undulating, mesh, porous, semi-porous, dimpled and/or textured to facilitate engagement with tether 130.

Figure 13:
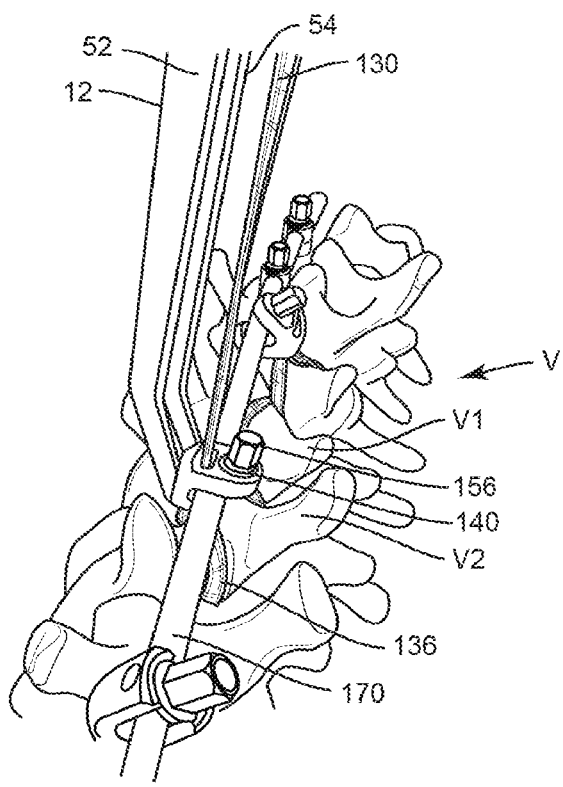
FIG. 13 is a break away view of one embodiment of components of a surgical system in accordance with the principles of the present disclosure disposed with vertebrae.
Figure 14:
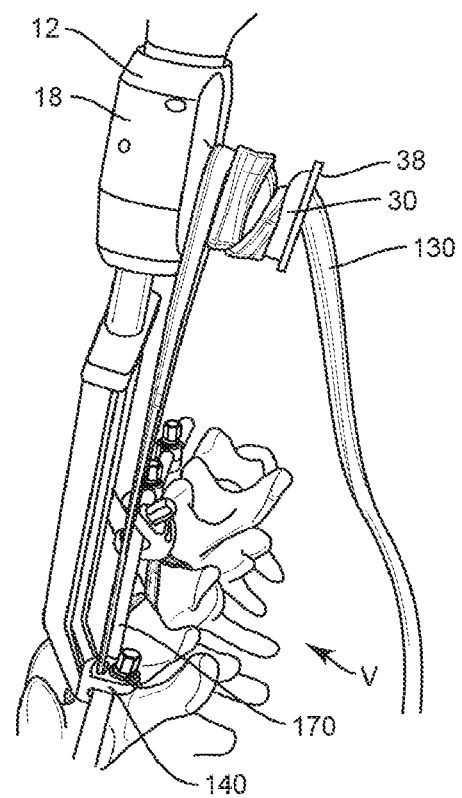
FIG. 14 is a break away view of the components and vertebrae shown in FIG. 13.
Figure 15:
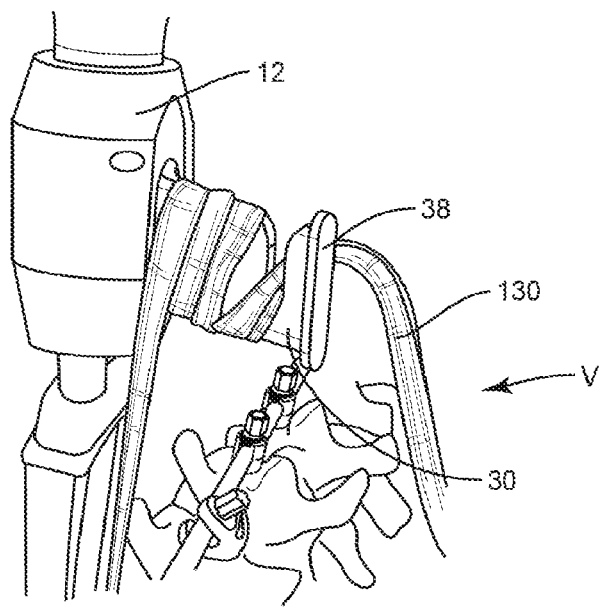
FIG. 15 is a break away view of the components and vertebrae shown in FIG. 13.
Figure 16:
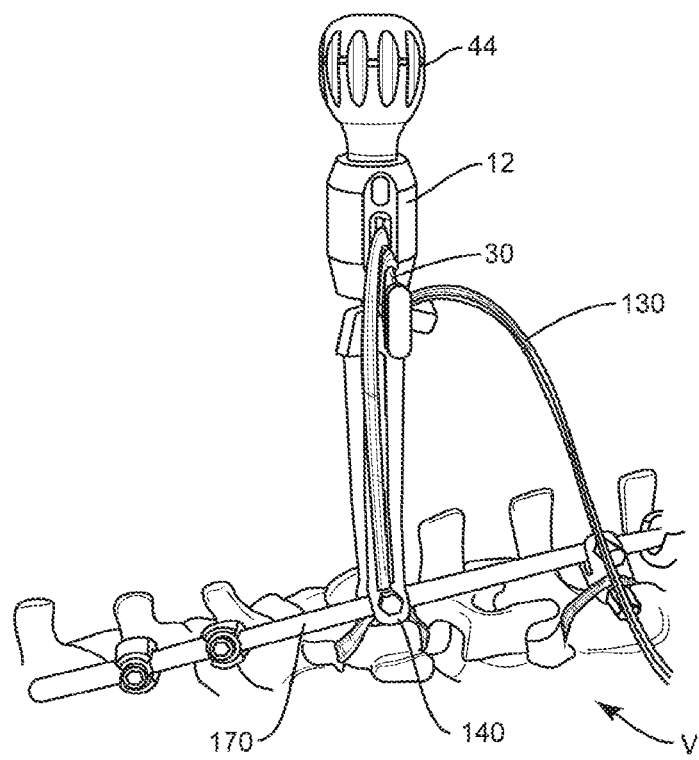
FIG. 16 is a perspective view of the components and vertebrae shown in FIG. 13.

Body 142 includes a surface 148 defining a cavity 150 configured for disposal of tether 130. In some embodiments, cavity 150 is disposed in alignment, offset or staggered from passageway 146. In some embodiments, opening 150 may have various cross section configurations, such as, for example, oval, oblong, triangular, rectangular, square, polygonal, irregular, uniform, non-uniform, variable and/or tapered. In some embodiments, surface 148 may include gripping elements or surfaces, such as, for example, rough, arcuate, undulating, mesh, porous, semi-porous, dimpled and/or textured to facilitate engagement with tether 130. Body 142 includes a surface 152 that defines a cavity, such as, for example, an opening 154. Opening 154 is configured for disposal of a coupling member, such as, for example, a set screw 156 (FIG. 13).

Body 142 includes a surface 160 that defines a passageway 162. Passageway 162 has an oblong configuration and extends through the body. In some embodiments, passageway 162 may have alternate cross section configurations, such as, for example, oval, cylindrical, triangular, square, polygonal, irregular, uniform, non-uniform, offset, staggered, undulating, arcuate, variable and/or tapered. Passageway 162 is configured for disposal of spinal rod 170 such that connector 140 can be mounted with spinal rod 170, as described herein.

Body 142 includes a mating surface 164 that defines cavities, such as, for example, mating slots configured to mate with tabs 72, 94 to facilitate connection of tensioner 12 with connector 140, as described herein. In some embodiments, spinal correction system 10 may include one or a plurality of implant connectors spaced apart and disposed along a spinal implant, such as, for example, spinal rod 170, which may be relatively disposed in a side by side, irregular, uniform, non-uniform, offset and/or staggered orientation or arrangement, along one or a plurality of spinal rods. In some embodiments, spinal rod 170 extends along one or a plurality of vertebra, as described herein. In some embodiments, spinal correction system 10 may include one or a plurality of spinal rods 170, which may be relatively disposed in a side by side, irregular, uniform, non-uniform, offset and/or staggered orientation or arrangement.

In assembly, operation and use, spinal correction system 10, similar to the systems and methods described herein, is employed with a surgical procedure, such as, for example, a correction treatment of an affected portion of a spine, for example, a correction treatment to treat adolescent idiopathic scoliosis and/or Scheuermann's kyphosis of a spine. In some embodiments, one or all of the components of spinal correction system 10 can be delivered or implanted as a pre-assembled device or can be assembled in situ. Spinal correction system 10 may be completely or partially revised, removed or replaced.

In use, to treat a selected section of vertebrae V, as shown in FIGS. 13-16, a medical practitioner obtains access to a surgical site including vertebrae V in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal correction system 10. A preparation instrument (not shown) can be employed to prepare tissue surfaces of vertebrae V, as well as for aspiration and irrigation of a surgical region.

Tether 130 is delivered along the surgical pathway to a surgical site adjacent vertebrae V. Tether 130 is disposed with vertebrae V. In one embodiment, as shown in FIGS. 13-16, a loop 136 of tether 130 is disposed about a transverse process of a vertebra V2 by passing end 132 continuously about the transverse process. This configuration fixes and/or attaches end 132 with the transverse process and/or lamina.

Upon disposal of end 132 with vertebra V2, tether 130 is disposed with connector 140. Tether 130 is threaded through cavity 150, passageway 162 and passageway 146. Spinal rod 170 is disposed with passageway 162 and reduced with connector 140 to vertebrae V. Set screw 156 is engaged with opening 154 to fix and/or provisionally fix spinal rod 170 with connector 140 and tether 130.

Arms 52, 54 of tensioner 12 are disposed adjacent connector 140. Lock 100 is rotated from a closed orientation, as described herein, in the direction shown by arrow A in FIG. 10, such that lock 100 translates along the engagement portion of arm 54 to engage barbs 88. Rotation of lock 100 causes arm 52 to rotate and/or pivot about hinge 68, in the direction shown by arrow B in FIG. 10, relative to arm 54 to dispose tensioner 12 in an open orientation, as described herein.

Mating tabs 72, 94 are aligned with the mating slots of connector 140. Lock 100 is rotated, in the direction shown by arrow C in FIG. 10, such that lock 100 translates from barbs 88 along the engagement portion of arm 54 to engage notch 86. Tabs 72, 94 rotate into engagement with the slots of connector 140 for releasable fixation and/or provisional fixation of tensioner 12 with connector 140, as shown in FIGS. 1, 13-16. Tensioner 12 is disposed in a closed orientation with connector 140.

End 134 of tether 130 extends from passageway 146. End 134 is drawn towards projection 30 and folded and/or rotated about the surface of projection 30 such that tether 130 is wound and/or wrapped around projection 30, as shown in FIGS. 12 and 13-16. A portion of end 134 is disposed with slot 34 to engage the surface defining slot 34 such that tether 130 is attached with and/or provisionally locked with tensioner 12. This configuration facilitates fixation of tether 130 with projection 30 during tensioning, which includes increasing and decreasing tension in tether 130.

Extensions 38*a*, 38*b* prevent and/or limit lateral movement of tether 130 to resist and/or prevent tether 130 from disengaging and/or slipping from the surface of projection 30. In some embodiments, the tension and/or tensile force applied to tether 130 and/or corrective forces applied to vertebrae V can be increased by rotating knob 44, in a clockwise direction shown by arrow E in FIG. 12. As such, the threaded engagement of carriage 18 with shaft 96, as described herein, causes axial translation of carriage 18 along axis X1 and relative to shaft 96, in the direction shown by arrow F in FIG. 12. Carriage 18 is translated relative to arms 52, 54 and the spinal construct, which includes connector 140 and spinal rod 170. Carriage 18 draws tether 130 to apply a tensioning force to tether 130. This configuration tensions tether 130 about vertebra V2 and tensions the spinal construct for attachment with vertebrae V and/or to apply corrective treatment to vertebrae V.

In some embodiments, the tension and/or tensile force applied to tether 130 and/or corrective forces applied to vertebrae V can be decreased by rotating knob 44, in a counter clockwise direction shown by arrow G in FIG. 12, to release tension. Carriage 18 threadably engages shaft 96 such that carriage 18 axially translates along axis X1 and relative to shaft 96, in the direction shown by arrow H in FIG. 12. Carriage 18 is translated relative to arms 52, 54 toward the spinal construct. This configuration releases tension in tether 130 and/or to adjust corrective treatment to vertebrae V.

In some embodiments, lock 100 is rotated from the closed orientation and locking of arms 52, 54 with connector 140 to the open orientation, as described herein. Rotation of lock 100 causes arms 52, 54 to relatively rotate and/or pivot about hinge 68 and release tabs 72, 94 from the slots of connector 140. Connector 140 is released from tensioner 12.

In some embodiments, spinal correction system 10 includes a second spinal rod (not shown) delivered along the surgical pathway to the surgical site adjacent a contra-lateral side of vertebrae V. The second spinal rod is connected with the contra-lateral side of vertebrae V via one or more tethers 130, similar to spinal rod 170 described herein. Spinal rod 170 and the second spinal rod are fixed with vertebrae V in a side by side orientation and/or bi-lateral arrangement to stabilize vertebrae V and affect growth for a correction treatment to treat spine pathologies, as described herein.

Upon completion of the procedure, the surgical instruments, assemblies and non-implanted components of spinal correction system 10 are removed from the surgical site and the incision is closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10.

In some embodiments, spinal correction system 10 includes an agent, which may be disposed, packed, coated or layered within, on or about the components and/or surfaces of spinal correction system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 may be used to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   a first member including a shaft and a projection extending from the shaft, the projection including opposing inner surfaces that define a slot therebetween, the inner surfaces being engageable with a longitudinal member disposed in the slot to fix the longitudinal member with the first member, the inner surfaces being fixed relative to the shaft; and
   a second member including first and second arms, the arms each including a mating element configured to engage a spinal construct, the first arm being pivotably connected with the second arm to move the arms between a closed orientation in which the mating elements are a first distance apart and an open orientation in which the mating elements are an increased second distance apart,
   wherein the first member is axially translatable relative to the second member in a first direction to tension the longitudinal member and in a second direction to release tension from the longitudinal member.

2. A surgical instrument as recited in claim 1, wherein the shaft defines a first longitudinal axis, the slot defining a second longitudinal axis, the second longitudinal axis extending parallel to the first longitudinal axis.

3. A surgical instrument as recited in claim 1, wherein the shaft defines a first longitudinal axis, the slot defining a second longitudinal axis, the second longitudinal axis extending parallel to the first longitudinal axis such that the second longitudinal axis is offset from the first longitudinal axis.

4. A surgical instrument as recited in claim 1, wherein the slot extends through a top surface of the projection without extending through an opposite bottom surface of the projection.

5. A surgical instrument as recited in claim 1, wherein the arms are biased to the open orientation by a biasing member.

6. A surgical instrument as recited in claim 5, wherein the biasing member is a spring having a first end that directly engages the first arm and a second end that directly engages the second arm.

7. A surgical instrument as recited in claim 1, wherein the inner surfaces are permanently fixed relative to the shaft.

8. A surgical instrument as recited in claim 1, wherein the second member includes a lock to fix the first arm relative to the second arm.

9. A surgical instrument as recited in claim 8, wherein the second arm includes a notch configured to engage the lock.

10. A surgical instrument as recited in claim 8, wherein the second arm includes a barb configured to limit movement of the lock.

11. A surgical instrument comprising:
    a first member including a shaft and a projection extending from the shaft, the projection including opposing inner surfaces that define a slot therebetween, the inner surfaces being engageable with a longitudinal member to fix the longitudinal member with the first member; and
    a second member including first and second arms, the arms each including a mating element configured to engage a spinal construct, the first arm being pivotably connected with the second arm to move the arms between a closed orientation in which the mating elements are a first distance apart and an open orientation in which the mating elements are an increased second distance apart, the second member including a lock to fix the first arm relative to the second arm, the second arm including a barb configured to limit movement of the lock,
    wherein the first member is axially translatable relative to the second member in a first direction to tension the longitudinal member and in a second direction to release tension from the longitudinal member.

12. A surgical instrument as recited in claim 11, wherein the shaft defines a first longitudinal axis, the slot defining a second longitudinal axis, the second longitudinal axis extending parallel to the first longitudinal axis.

13. A surgical instrument as recited in claim 11, wherein the shaft defines a first longitudinal axis, the slot defining a second longitudinal axis, the second longitudinal axis extending parallel to the first longitudinal axis such that the second longitudinal axis is offset from the first longitudinal axis.

14. A surgical instrument as recited in claim 11, wherein the slot extends through a top surface of the projection without extending through an opposite bottom surface of the projection.

15. A surgical instrument as recited in claim 11, wherein the arms are biased to the open orientation by a biasing member.

16. A surgical instrument comprising:
- a first member including a shaft and a projection extending from the shaft, the projection including opposing inner surfaces that define a slot therebetween, the inner surfaces being engageable with a longitudinal member to fix the longitudinal member with the first member;
- a second member including first and second arms, the arms each including a mating element configured to engage a spinal construct, the first arm being pivotably connected with the second arm to move the arms between a closed orientation in which the mating elements are a first distance apart and an open orientation in which the mating elements are an increased second distance apart; and
- a rotatable actuator that axially translates the first member relative to the second member in a first direction to tension the longitudinal member and in a second direction to release tension from the longitudinal member, the projection being positioned between the actuator and the second member.

17. A surgical instrument as recited in claim 16, wherein the actuator is spaced apart from the second member.

18. A surgical instrument as recited in claim 16, wherein the shaft defines a longitudinal axis, the actuator being rotatable about the longitudinal axis.

19. A surgical instrument as recited in claim 16, wherein the surgical instrument has a maximum length defined by a distance from a proximal end of the actuator to distal ends of the arms.

20. A surgical instrument as recited in claim 16, wherein the inner surfaces are permanently fixed relative to the shaft.

* * * * *